United States Patent
AlTunisi et al.

(10) Patent No.: US 11,614,429 B1
(45) Date of Patent: Mar. 28, 2023

(54) UNIVERSAL AUTONOMOUS SAFETY GUARD

(71) Applicant: Saudi Arabian Oil Company, Dhahran (SA)

(72) Inventors: Ahmed Mohammed AlTunisi, Dhahran (SA); Saleh Magboul Al-Ghamdi, Dammam (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 17/480,340

(22) Filed: Sep. 21, 2021

(51) Int. Cl.
  *G01N 33/00* (2006.01)
  *G01N 1/22* (2006.01)

(52) U.S. Cl.
  CPC ....... *G01N 33/0006* (2013.01); *G01N 1/2247* (2013.01)

(58) Field of Classification Search
  CPC ............... G01N 33/006; G01N 33/007; G01N 2033/0072; G01N 2035/0403; G01N 2035/0405
  See application file for complete search history.

(56) References Cited

U.S. PATENT DOCUMENTS

| | | | | |
|---|---|---|---|---|
| 3,693,401 A | * | 9/1972 | Purt | B65D 83/28 73/1.05 |
| 4,279,142 A | * | 7/1981 | McIntyre | G01N 27/4175 73/1.06 |
| 4,462,244 A | * | 7/1984 | Lee | G08B 29/145 73/1.05 |
| 4,489,590 A | * | 12/1984 | Hadden | G01N 33/0006 73/1.04 |
| 4,590,789 A | | 5/1986 | Kunze | |

(Continued)

FOREIGN PATENT DOCUMENTS

| CN | 110988274 A | 4/2020 |
|---|---|---|
| CN | 111033252 A | 4/2020 |

(Continued)

OTHER PUBLICATIONS

"MSA'S Revolutionary TruCal Gas Sensor Technology", https://us.msasafety.com/trucal, Accessed Mar. 16, 2021.

*Primary Examiner* — David A. Rogers
(74) *Attorney, Agent, or Firm* — Dinsmore & Shohl LLP (57) ABSTRACT

A universal safety guard is provided. The guard may comprise a housing comprising an adapter coupling end, a dual mode chamber, a calibration gas port, and an ambient air end. The guard may also comprise an assembly configurable in a sensing position, in which ambient air may be admitted into the chamber, and a calibration position, in which calibration gas may be admitted into the chamber and the ambient air is blocked from reaching the chamber. The guard may comprise a detector adapter comprising a calibration housing fitting at one end and a gas detector fitting at an opposite end. The calibration housing fitting may comprise a static circumferential sealing interface that hermetically engages the adapter coupling end. The gas detector fitting may comprise a dynamic inner circumferential sealing interface for hermetic engagement with a gas detector comprising an outer sealing interface that complements the dynamic inner circumferential sealing interface.

20 Claims, 4 Drawing Sheets

(56) References Cited

U.S. PATENT DOCUMENTS

| | | | | |
|---|---|---|---|---|
| 5,170,148 | A * | 12/1992 | Duggan | G08B 29/145 340/693.5 |
| 5,523,744 | A * | 6/1996 | Wieser | G08B 29/145 340/630 |
| 5,611,620 | A * | 3/1997 | Wantz | G08B 29/145 374/1 |
| 5,670,946 | A * | 9/1997 | Ellwood | G08B 29/145 340/630 |
| 6,015,230 | A * | 1/2000 | Wantz | G08B 29/145 374/1 |
| 6,423,962 | B1 * | 7/2002 | Pepper | G08B 29/145 340/630 |
| 6,640,608 | B2 * | 11/2003 | Pepper | G08B 29/145 340/630 |
| 6,741,181 | B2 * | 5/2004 | Skaggs | G08B 17/113 73/40.5 R |
| 6,769,285 | B2 * | 8/2004 | Schneider | G08B 29/145 73/1.06 |
| 6,803,853 | B2 * | 10/2004 | Schneider | G08B 29/145 340/506 |
| 6,918,281 | B2 * | 7/2005 | Sussman | G01N 33/0006 73/1.05 |
| 7,225,661 | B2 * | 6/2007 | Hong | G01N 33/0006 73/1.02 |
| 7,401,493 | B2 * | 7/2008 | Forrest | G01N 33/0006 73/1.06 |
| 7,581,425 | B2 * | 9/2009 | Forrest | G01N 33/0006 73/1.06 |
| 7,587,926 | B2 * | 9/2009 | Ackerman | B65D 83/30 73/1.02 |
| 8,353,625 | B1 * | 1/2013 | Feiter | G08B 29/145 374/121 |
| 8,454,228 | B2 * | 6/2013 | Skinner | G01K 15/00 374/208 |
| 8,973,211 | B2 * | 3/2015 | Rote | A47L 9/08 15/345 |
| D779,352 | S * | 2/2017 | Scarder | D10/104.1 |
| 2008/0224847 | A1 * | 9/2008 | Pepper | G08B 29/145 340/514 |
| 2020/0309647 | A1 | 10/2020 | Smedsrud et al. | |
| 2021/0262997 | A1 * | 8/2021 | Alsalman | G01N 33/007 |

FOREIGN PATENT DOCUMENTS

| | | |
|---|---|---|
| CN | 211978855 U | 11/2020 |
| EP | 0016351 A1 | 10/1980 |
| JP | 2001133367 A | 5/2001 |
| KR | 101995993 B1 | 7/2019 |

* cited by examiner

UNIVERSAL AUTONOMOUS SAFETY GUARD

BACKGROUND

The present disclosure relates to universal safety guards, and more particularly, to universal safety guards that permit calibration of gas detectors having different dimensions with the use of adjustable detector adapters that enable engagement of the universal safety guards with these gas detectors. Typically, gas detectors may not be built according to a uniform set of standards, as gas detector manufacturers may choose different dimensional criteria and be constrained by various design choices, cost factors, etc. As such, calibration of these gas detectors may require the use of calibration systems that vary widely in terms of component dimensions, component weights, component costs, etc. Thus, conventional calibration techniques are inconvenient and inefficient.

BRIEF SUMMARY

The subject matter of the present disclosure addresses and overcomes the deficiencies of current gas detector calibration systems. The present disclosure describes a universal safety guard that enables the calibration of gas detectors built according to varying dimensional specifications. In particular, the universal safety guard of the present disclosure may comprise an adjustable detector adapter that hermetically engages with and conforms to the specific designs and dimensions of conventional gas detectors. The universal safety guard of the present disclosure may also form a tight seal with the gas detectors, which ensures that calibration gas that enters the universal safety guard from an external environment does not escape from the universal safety guard into the external environment. The universal safety guard of the present disclosure may also comprise a real-time obstruction sensing mechanism that determines instances in which one or more filters located within the safety guards are obstructed. The safety guard also may also comprise a cleaning mechanism that removes or purges the obstructions from the one or more filters.

In accordance with one embodiment of the present disclosure, a universal safety guard may comprise a calibration housing and a calibration valve assembly. The calibration housing may comprise an adapter coupling end, a dual mode chamber, a calibration gas port, and an ambient air end comprising an ambient air aperture. The dual mode chamber may be located between the adapter coupling end and the ambient air end of the calibration housing. The calibration valve assembly may be disposed in the dual mode chamber of the calibration housing and may be configurable in a sensing position and a calibration position. The calibration valve assembly, when configured in the sensing position, may admit ambient air through the ambient air aperture into the dual mode chamber, and when configured in the calibration position, may admit calibration gas into the dual mode chamber, through the calibration gas port, and may block the ambient air from reaching the dual mode chamber.

The universal safety guard may further comprise a detector adapter that comprises a hermetic gas passage body portion extending from a calibration housing fitting at one end of the detector adapter to a gas detector fitting at an opposite end of the detector adapter. The calibration housing fitting may comprise a static circumferential sealing interface that hermetically engages the adapter coupling end of the calibration housing and the gas detector fitting may comprise a dynamic inner circumferential sealing interface for hermetic engagement with a gas detector comprising an outer sealing interface that complements the dynamic inner circumferential sealing interface of the gas detector fitting.

BRIEF DESCRIPTION OF THE DRAWINGS

The following detailed description of specific embodiments of the present disclosure can be best understood when read in conjunction with the following drawings, where like structure is indicated with like reference numerals and in which.

DETAILED DESCRIPTION

Gas detectors are installed in various locations within residential and commercial buildings and operate to detect the presence of a threshold concentration of one or more gases in an ambient environment. Various factors may adversely affect the accuracy of these detectors, e.g., dirt, dust, water, moisture, extreme temperature variations in the environment in which the gas detectors are positioned, and so forth. As such, these detectors are calibrated periodically to determine whether they possess the capability to accurately determine threshold volumes and concentrations of gases specific by, e.g., a manufacturer, a government agency, etc. If these detectors are able to so do, they are classified as operating as intended. However, if the gas detectors are unable to accurately determine the volumes and concentrations of certain gases (e.g., calibration gases), the gas detectors may require repair and replacement.

As gas detectors may be built by different manufacturers, these detectors may be vary in design and dimensions. As such, there is a need for a universal safety guard that permits calibration of gas detectors built according to varying designs and dimensional specifications. As described throughout, the present disclosure describes universal safety guards that may comprise adjustable detector adapters, which are designed to engage with gas detectors having different dimensions and dimensions, and calibration of each of these detectors using the adjustable detector adapters. The adjustable detector adapters may form a tight seal with the gas detectors, thereby ensuring that, during gas detector calibration, a test gas (e.g., calibration gas) does not escape from the universal safety guard into the environment that is external to the universal safety guard. Embodiments of the universal safety guards described in the present disclosure may comprise a real-time obstruction sensing mechanism that determines instances in which filters within the safety guards are obstructed. Embodiments of the universal safety guards may also comprise a cleaning mechanism that removes or purges these obstructions in real-time.

Figure 1:
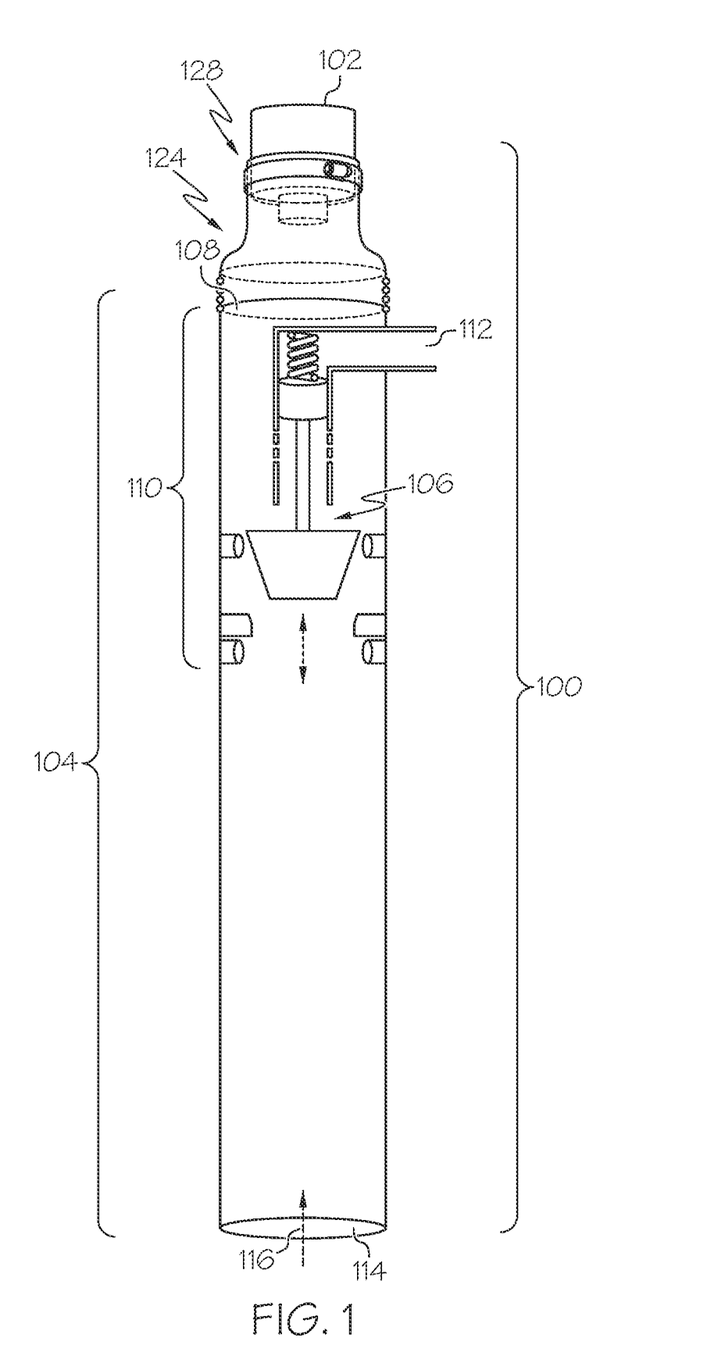
FIG. 1 is a schematic depiction of the universal safety guard engaged with a gas detector that is external to the universal safety guard, according to one or more embodiments described and illustrated herein.
Figure 2:
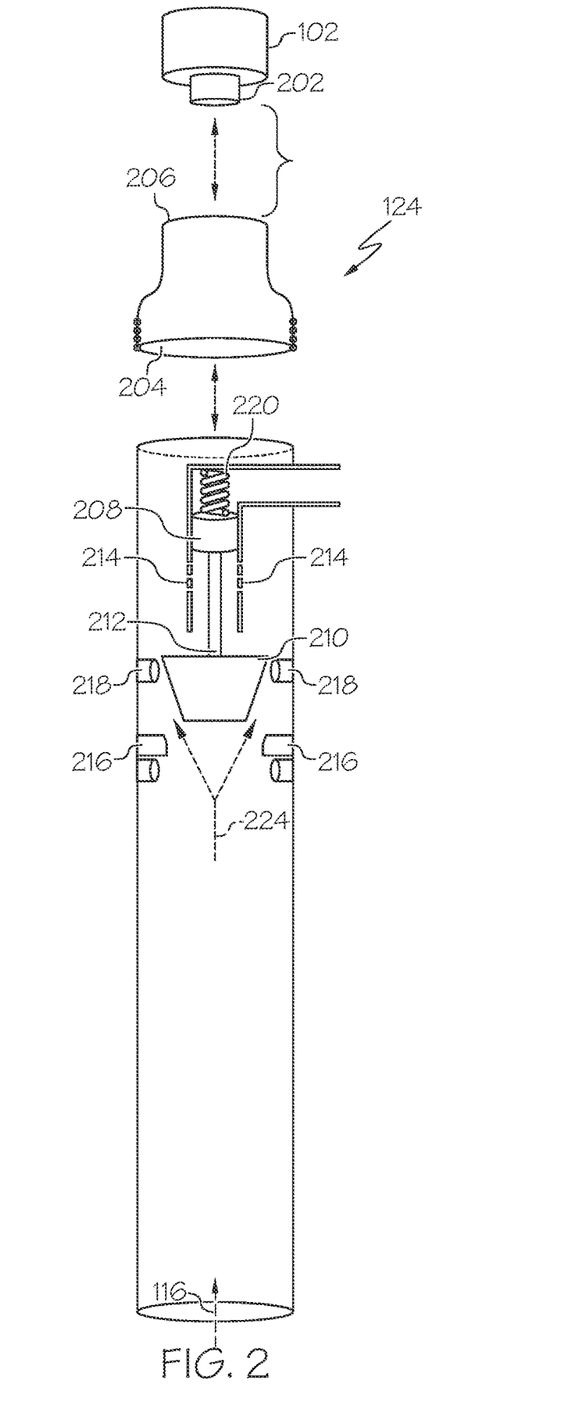
FIG. 2 is a schematic depiction of the calibration valve assembly being configured in a sensing position, according to one or more embodiments described and illustrated herein.
Figure 3:
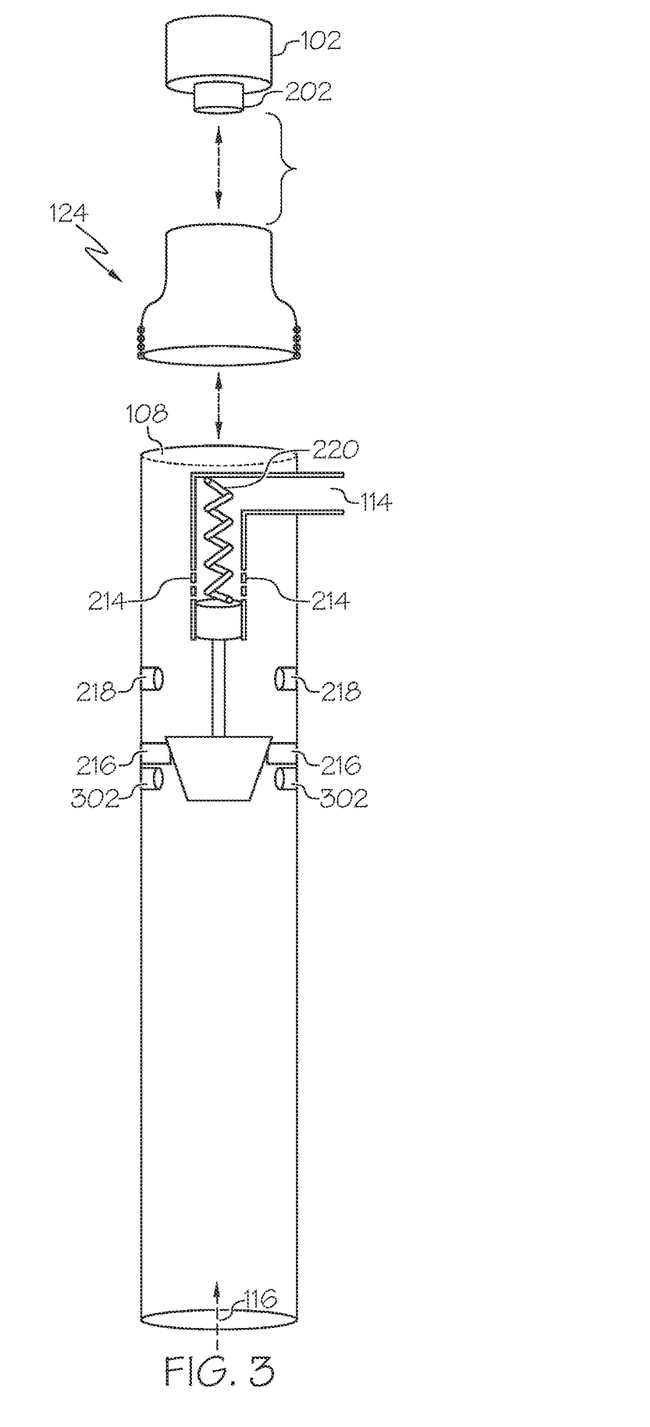
FIG. 3 is a schematic depiction of the calibration valve assembly being configured in a calibration position, according to one or more embodiments described and illustrated herein.
Figure 4:
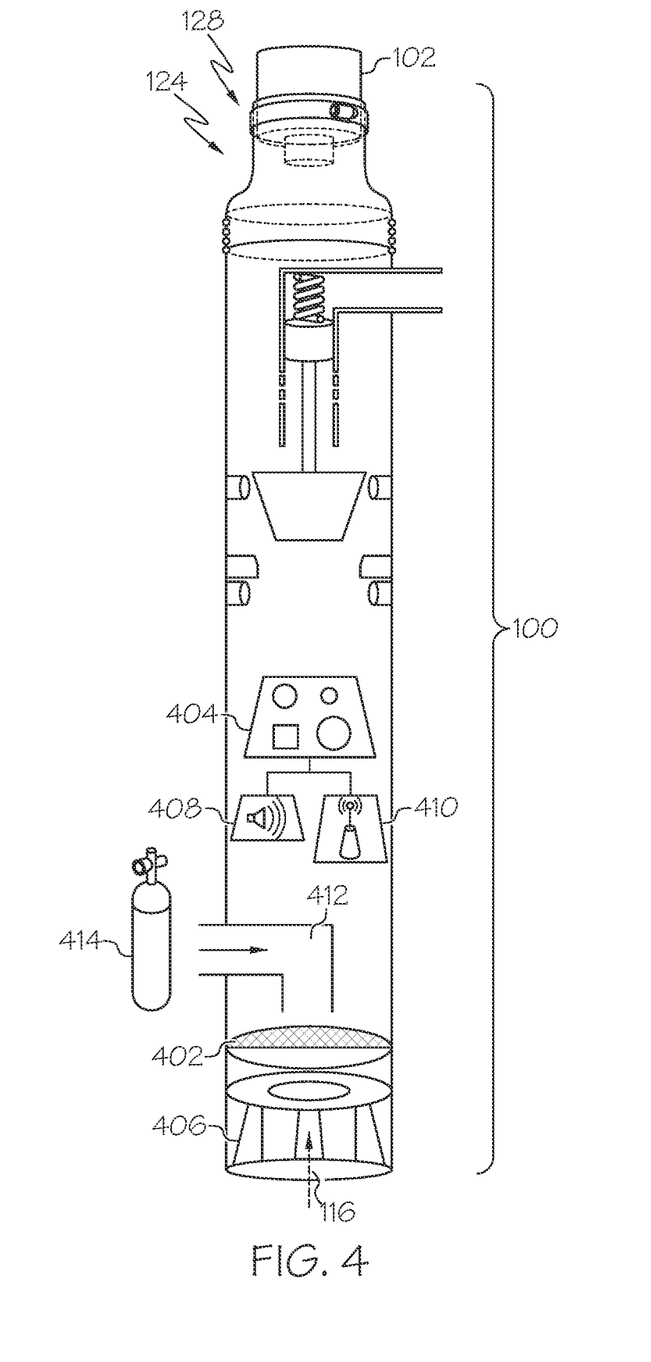
FIG. 4 is a schematic depiction of various components of the universal safety guard that facilitate the maintenance and cleaning of the universal safety guard, according to one or more embodiments described and illustrated herein.

Referring initially to FIGS. 1-4, embodiments of a universal safety guard 100 and various associated components for enabling the calibration of various gas detectors are schematically depicted. FIG. 1 is a schematic depiction of the universal safety guard 100 engaged with a gas detector 102 that is external to the universal safety guard 100. FIG. 2 is a schematic depiction of various components of the universal safety guard 100 and the manner in which the universal safety guard 100 permits ambient air to pass through areas within the universal safety guard 100 and reach the gas detector 102. FIG. 3 is a schematic depiction of various components of the universal safety guard 100 and the manner in which the universal safety guard 100 permits calibration gas to pass through the universal safety guard 100 and reach the gas detector 102 while blocking ambient air from entering the universal safety guard 100. FIG. 4 is a schematic depiction of various components of the universal safety guard 100 and the manner in which one or more of these components are cleaned by universal safety guard 100.

Referring initially to FIG. 1, the universal safety guard 100, which enables calibration of various gas detectors (e.g., the gas detector 102), may comprise a calibration housing 104 and a calibration valve assembly 106. The calibration housing 104 may comprise an adapter coupling end 108, a dual mode chamber 110, a calibration gas port 112, and an ambient air end 114 comprising an ambient air aperture 116. The dual mode chamber 110 may be located between the adapter coupling end 108 and the ambient air end 114 of the calibration housing 104. The calibration valve assembly 106 may be disposed in the dual mode chamber 110 of the calibration housing 104 and may be configurable in a sensing position and a calibration position. In embodiments, the calibration valve assembly 106, when configured in the sensing position, may admit ambient air through the ambient air aperture 116 into the dual mode chamber 110. Additionally, when configured in the calibration position, the calibration valve assembly 106 may admit calibration gas into the dual mode chamber 110 and block the ambient air from reaching the dual mode chamber 110.

In embodiments, the universal safety guard 100 may further comprise a detector adapter 124. The detector adapter 124 may comprise a hermetic gas passage body portion extending from a calibration housing fitting 204 (as indicated in FIG. 2) at one end of the detector adapter 124 to a gas detector fitting 206 (as indicated in FIG. 2) at an opposite end of the detector adapter 124. The calibration housing fitting 204 may comprise a static circumferential sealing interface that hermetically engages the adapter coupling end 108 of the calibration housing 104. Additionally, the gas detector fitting 206 may comprise a dynamic inner circumferential sealing interface for hermetic engagement with the gas detector 102. The gas detector 102 may comprise an outer sealing interface that complements the dynamic inner circumferential sealing interface of the gas detector fitting 206.

In embodiments, the gas detector fitting 206 may expand in diameter to tightly fit around the outer perimeters of various gas detectors having different dimensions. In embodiments, while the diameter of the gas detector fitting 206 may change to conform to the outer perimeters of these gas detectors, the diameter of the calibration housing fitting 204 may remain static. In other words, the changes in the diameter of the gas detector fitting 206 of the detector adapter 124 will not affect the diameter of the calibration housing fitting 204. It is noted that the hermetic gas body portion of the detector adapter 124 may comprise a uniform elastomeric polymer composition, e.g., polybutadiene, chloroprene rubber, styrene-butadiene rubber, etc.

In embodiments, the calibration housing fitting 204 of the detector adapter 124 and the adapter coupling end 108 of the calibration housing 104 may comprise complementary threaded portions. For example, in embodiments, female threaded portions may be disposed on the calibration housing fitting 204 of the detector adapter 124 that are configured to mate with complementary male threaded portions disposed on the adapter coupling end 108 of the calibration housing 104. In other embodiments, male threaded portions may be disposed on the calibration housing fitting 204 of the detector adapter 124 that are configured to mate with complementary female threaded portions disposed on the adapter coupling end 108 of the calibration housing 104.

In embodiments, the hermetic engagement between the static circumferential sealing interface of the detector adapter 124 and the adapter coupling end 108 of the calibration housing 104 may be based on a snap-fit feature. For example, in operation, the static circumferential sealing interface of the detector adapter 124 may be positioned around an outer perimeter of the adapter coupling end 108. Thereafter, downward pressure may be applied on the detector adapter 124 in order to mechanically couple the detector adapter 124 to the calibration housing 104. In this way, the detector adapter 124 may be "snap fitted" to the calibration housing 104. In embodiments, an upward pressure applied on the detector adapter 124 may disengage and mechanically decouple the detector adapter 124 from the calibration housing 104.

In embodiments, the hermetic engagement between the static circumferential sealing interface of the detector adapter 124 and the adapter coupling end 108 of the calibration housing 104 may also be based on a twist-to-lock feature. For example, in operation, the static circumferential sealing interface of the detector adapter 124 may be positioned around an outer perimeter of the adapter coupling end 108. Thereafter, downward pressure may be applied on the detector adapter 124 in combination with a clockwise rotational movement of the detector adapter 124 relative to the adapter coupling end 108 in order to mechanically couple the detector adapter 124 to the calibration housing 104. In this way, the detector adapter 124 may be coupled to the calibration housing 104 using the twist-to-lock feature. In embodiments, upward pressure applied on the detector adapter 124 in combination with a counter-clockwise rotation of the detector adapter 124 may disengage and mechanically decouple the detector adapter 124 from the calibration housing 104.

In embodiments, the hermetic engagement between the static circumferential sealing interface of the detector adapter 124 and the adapter coupling end 108 of the calibration housing 104 may also be based on a press fit feature. For example, the static circumferential sealing interface of the detector adapter 124 may comprise multiple protrusions, e.g., cylindrical protrusions, that extend outwards from multiple portions of the calibration housing fitting 204. These protrusions may be disposed within corresponding protrusion receiving apertures located on the adapter coupling end 108 of the calibration housing fitting 204. For example, the protrusions extending outwards from multiple portions of the calibration housing fitting 204 may be aligned with the corresponding protrusion receiving apertures on the adapter coupling end 108 and downward pressure may be applied on the detector adapter 124 such that the protrusions of the calibration housing fitting 204 may be pushed into or disposed within the corresponding protrusion receiving apertures. In other embodiments, the adapter coupling end 108 of the calibration housing 104 may comprise multiple protrusions, e.g., cylindrical protrusions, that extend outwards from multiple portions of the adapter coupling end 108. These protrusions may be disposed within corresponding protrusion receiving apertures located on the calibration housing fitting 204 of the detector adapter 124. For example, these protrusions may be aligned with the corresponding protrusion receiving apertures on the calibration housing fitting 204 and downward pressure may be applied on the detector adapter 124 such that the protrusions may be pushed into or disposed within the corresponding protrusion receiving apertures on the calibration housing fitting 204. In this way, the detector adapter 124 may be coupled to the calibration housing 104 using the press fit feature. In embodiments, upward pressure applied on the detector adapter 124 may disengage and mechanically decouple the detector adapter 124 from the calibration housing 104.

In embodiments, the universal safety guard 100 may further comprise an adjustable ring clamp 128. The adjustable ring clamp 128 may comprise a maximum clamping diameter that is larger than an outside diameter of the gas detector fitting 206 in the expanded state, and a minimum clamping diameter that is smaller than the outside diameter of the gas detector fitting 206 in the resting state. In embodiments, the adjustable ring clamp 128 may comprise a maximum clamping diameter that is larger than an outside diameter of the gas detector fitting 206 in the resting state. The adjustable ring clamp 128 may be configured to deliver an inwardly directed radial clamping force. The delivered clamping force may prevent any dirt or debris from entering the detector adapter 124 during calibration of the gas detector 102. In embodiments, the adjustable ring clamp 128 may comprise a knob. Adjusting the knob may enable increasing the inwardly directed clamping force delivered by the adjustable ring clamp 128 on the outer surface of the detector adapter 124.

FIG. 2 is a schematic depiction of the calibration valve assembly 106 being configured in a sensing position, according to one or more embodiments described and illustrated herein. Referring to FIG. 2, the gas detector 102 may comprise a gas sensor 202 that is configured to detect concentrations and volumes of various types of gases. Still referring to FIG. 2, in embodiments, regarding the detector adapter 124, the hermetic gas passage body portion of the detector adapter 124 steps down from a larger diameter portion at the calibration housing fitting 204 to a smaller diameter portion at the gas detector fitting 206, or from a larger diameter portion at the gas detector fitting 206 to a smaller diameter portion at the calibration housing fitting 204. Additionally, the body portion of the detector adapter 124 may comprise a uniform elastomeric polymer composition extending from the calibration housing fitting 204 to the smaller diameter portion at the gas detector fitting 206. In embodiments, the dynamic inner circumferential sealing interface of the gas detector fitting 206 may comprise an expandable sleeve that transitions from a resting state to an expanded state where the gas detector fitting 206 may exert an inwardly directed radial force.

In embodiments, the resting state of the expandable sleeve may be characterized by an inside diameter that is less than about 5.5 centimeters. In embodiments, the resting state of the expandable sleeve may be characterized by an inside diameter that is between about 2.5 centimeters to about 5.5 centimeters. In embodiments, the expansion of the expandable sleeve of the gas detector fitting 206 may be isolated from the static circumferential sealing interface of the calibration housing fitting 204, such that diametrical changes at the dynamic inner circumferential sealing interface may not translate into diametrical changes at the static circumferential sealing interface. In embodiments, the expandable sleeve may function in the manner as described above by designing the detector adapter 124 with the step-down profile, as described above and illustrated in FIG. 2, and manufacturing it from a flexible elastomeric polymer.

Additionally, in embodiments, the dynamic circumferential sealing interface of the gas detector fitting 206 may comprise a compressible sleeve that transitions from a resting state to a compressed state under the clamping force of the adjustable ring clamp 128 as described above and as illustrated in FIG. 1. In such embodiments, the gas detector fitting 206 may be designed to be slightly larger than the outside diameter of the hardware of the gas detector 102, and may be compressed into a sealed engagement with the hardware of the gas detector 102 with the aid of the adjustable ring clamp 128 or other similar hardware. In embodiments, the compression of the compressive sleeve of the gas detector fitting 206 may be isolated from the static circumferential sealing interface of the calibration housing fitting 204 such that diametrical changes at the dynamic inner circumferential sealing interface may not translate into diametrical changes at the static circumferential sealing interface.

In embodiments, the calibration valve assembly 106 may comprise a spring-loaded rod and plug assembly, which may comprise a calibration gas plug 208 and an ambient air plug 210 on opposite ends of a spring-loaded valve rod 212. The spring-loaded valve rod 212 and the calibration gas plug 208 may move along a valve passage to selectively admit calibration gas through a calibration gas admittance window 214 of the valve passage, as illustrated in FIG. 3 and described below. Specifically, the spring-loaded valve rod 212 is configured to advance the ambient air plug 210 into engagement with a valve stop 216 between the ambient air aperture 116 and the dual mode chamber 110 to block ambient air, while the calibration gas plug 208 is positioned to admit calibration gas through the calibration gas admittance window 214 of the valve passage. In embodiments, the calibration valve assembly 106 may further comprise one or more sensing-position limit switches 218 to enhance control of the movement of the spring-loaded valve rod 212 back and forth through the valve passage as the spring-loaded rod and plug assembly transitions back and forth between the sensing position, which is illustrated in FIG. 2, and the calibration position, which is illustrated in FIG. 3. It is noted that a valve actuator may be provided to facilitate the back and forth movement of the spring-loaded rod and plug assembly.

In embodiments, when the calibration valve assembly 106 is in the sensing position, the spring-loaded rod and plug assembly may be positioned such that a spring 220 with which the spring-loaded rod and plug assembly may be coupled or be configured to contact may be in a resting (e.g., non-extended) state. In the sensing position, ambient air may enter the calibration housing 104 through the ambient air aperture 116 and travel, through an ambient air gap 224, into the dual mode chamber 110. Additionally, the ambient air may travel from the dual mode chamber 110 and into the interior portion of the detector adapter 124. From the interior portion, the ambient air may travel to and contact the gas sensor 202. It is noted that, when in the sensing position, the calibration gas plug 208 may block any volume of calibration gas from entering the dual mode chamber 110. As such, in the sensing position, only ambient air may enter the dual mode chamber 110. When in the sensing position, the ambient air plug 210 may be positioned adjacent to one or more sensing-position limit switches 218, which may provide feedback or data related to the position of the ambient air plug 210 at any given time. The manner in which the sensing-position limit switches 218 may provide feedback or data relating to the position of the ambient air plug 210 is described below.

FIG. 3 is a schematic depiction of the calibration valve assembly 106 being configured in a calibration position, according to one or more embodiments described and illustrated herein. In embodiments, during the calibration, calibration gas may be released from, e.g., a calibration gas container or storage cylinder, and enter the calibration housing 104 through the calibration gas port 112. In embodiments, the calibration process may be initiated remotely. For example, through wired or wireless communication, a technician may control the release of calibration gas from the calibration gas storage tank (not shown) that may be positioned adjacent to the calibration gas port 112. An end of a calibration gas supply line (not shown) may be connected to the calibration gas storage tank and another end of the calibration gas supply line may be disposed in or positioned adjacent to the calibration gas port 112. It is noted that operation of calibration gas storage tank (e.g., releasing calibration gas and stopping the release of the calibration gas) may be controlled with a solenoid valve, which may initiate and stop the emission of calibration gas from the calibration gas storage tank. The calibration gas storage tank may be communicatively coupled to a microcontroller (not shown) that may be positioned adjacent to the calibration gas storage tank. In embodiments, the microcontroller or another comparable computing device may be controlled remotely.

During calibration, the calibration gas that enters the calibration gas port 112 may exert pressure on the calibration gas plug 208, causing the spring-loaded rod and plug assembly to move downward along the valve passage and engage with a valve stop 216 that is located between the ambient air aperture 116 and the dual mode chamber 110. As a result, the spring 220 may expand (e.g., the state of the spring 220 may change from a resting state to an active state). Additionally, during the calibration, if the ambient air plug 210 moves downwards along the valve passage but fails to engage with the valve stop 216, and the ambient air plug 210 is no longer in contact with or within a certain proximity of the sensing-position limit switches 218, the spring-loaded rod and plug assembly may be in a position that allows calibration gas to both enter the dual mode chamber 110 and possibly escape into the environment that is external to the calibration housing 104. In particular, the calibration gas that enters the dual mode chamber 110 may also exit the dual mode chamber 110 by travelling outside the dual mode chamber 110 through the ambient air gap 224 (as illustrated in FIG. 2) and exit the calibration housing 104 through the ambient air aperture 116 on the ambient air end 114 of the calibration housing 104.

As such, if the ambient air plug 210 fails to contact the valve stop 216 and is not detected by the calibration position limit switches 302 for a predetermined time period, while also failing to contact the sensing-position limit switches 218 for a predetermined time frame, an audio alarm may be generated by, e.g., a battery operated speaker (not shown) installed within the calibration housing 104. In this way, an individual may be alerted of the possibility of toxic test gas (e.g., calibration gas) that may exit the universal safety guard 100 and enter the environment that is external to the gas detector 102.

In embodiments, during the calibration process, pressure exerted by the calibration gas may be such that the spring-loaded valve rod 212 may advance the ambient air plug 210 into engagement with the valve stop 216 that is located between the ambient air aperture 116 and the dual mode chamber 110. Upon contact with the valve stop 216, the ambient air gap 224 through which ambient air may travel into the dual mode chamber 110 may be sealed, while the calibration gas may enter the dual mode chamber 110 via the calibration gas admittance window 214 of the valve passage. In this way, in the calibration position, as illustrated in FIG. 3, ambient air that enters the calibration housing 104 through the ambient air aperture 116 may be prevented from entering the dual mode chamber 110, while the calibration gas may be admitted into the dual mode chamber 110 through the calibration gas admittance window 214.

Upon completion of the calibration process, the supply of calibration gas may be stopped. As a result, the spring 220 may retract from the expanded state to the resting state, causing the spring-loaded valve rod 212 to advance upwards along the valve passage such that the ambient air plug 210 may be positioned adjacent to the sensing-position limit switches 218. In this way, the calibration valve assembly 106 may now return to the sensing position from the calibration position. In embodiments, if the ambient air plug 210 moves upwards but fails to contact the sensing-position limit switches 218 within a predetermined time frame, an audio alarm may be generated by, e.g., a battery operated speaker (not shown).

Referring to FIG. 4, the universal safety guard 100 may comprise an ambient air filter 402, a proximity sensor, and a filter maintenance controller 404. In embodiments, a liquid filter 406 may also be positioned underneath the ambient air filter 402. The liquid filter 406 may be a splash guard, while the ambient air filter 402 may be a dust guard. In embodiments, the ambient air filter 402 and the liquid filter 406 may be combined or fused such that the combined filter protects against the accumulation of both dust and liquids. As such, the amount of dust and liquid that may accumulate within the universal safety guard 100 is reduced. Consequently, the frequency with which maintenance personnel may have to clean the universal safety guard 100 may also be reduced. The combined safety guard may be particularly advantageous when the universal safety guard 100 is engaged with the gas detector 102, which may be positioned in a location that is not easily accessible by maintenance personnel. In embodiments, the combined filter may be made of a variety of materials, e.g., metallic, nonmetallic, transparent, non-transparent. etc. Additionally, the combined filter functions as a dust/splash guard and may be made of durable materials such as, for example, stainless steel, Glass Reinforced Plastic (GRP), and other comparable materials.

In embodiments, the proximity sensor may be a sound-based sensor 408 or an optical sensor 410. The proximity sensor may be utilized to detect presence of obstructions (e.g., dust, debris, etc.), which may have accumulated on the ambient air filter 402. In embodiments, multiple sensors may be used in combination, e.g., the sound-based sensor 408 and the optical sensor 410. In embodiments, the proximity sensor may be a laser based sensor, an ultrasonic sensor, or an IR sensor. In embodiments, the ambient air filter 402 may be positioned upstream of the ambient air aperture 116, between the dual mode chamber 110 and the ambient air aperture 116, or downstream of the ambient air aperture 116.

The proximity sensor may be positioned upstream of the ambient air filter 402, between the dual mode chamber 110 and the ambient air filter 402 and may be configured to measure a distance between a control position upstream of the ambient air filter 402 and an obstructed position downstream of the control position.

The proximity sensor may be configured to generate an obstruction signal that indicates an air flow obstruction downstream of the control position, and transmit the obstruction signal to the filter maintenance controller 404. Additionally, in embodiments, the filter maintenance controller 404 is configured to generate an obstruction alert upon receiving an obstruction signal indicating an air flow obstruction downstream of the control position, in the vicinity of the ambient air filter 402. In embodiments, the obstruction alert may be an audio alert, a visual alert, or an alert that is transmitted over a communications link. In embodiments, the filter maintenance controller 404 may be communicatively coupled to one or more external devices via a wired or wireless connection. The wireless communication may be based on various protocols such as 4-20 mA, FF, Bluetooth, LTE, Wireless HART, ISA100.11a, and so forth.

In embodiments, the sound-based sensor 408 or acoustic sensor may utilize sound propagation techniques to detect various objects. Depending on reflections received from the propagated sound waves that contact various objects, one or more obstructions associated with these objects may be detected. Additionally, the universal safety guard 100 may comprise a filter cleaning port 412 that may be in communication with a supply of purge gas. In embodiments, the purge gas may be compressed air that is dispensed from a purge gas cylinder 414 that is in communication with the filter cleaning port 412. In embodiments, the obstruction alert that is generated by the filter maintenance controller 404 may initiate a purge operation in which the purge gas (e.g., compressed air) may be transmitted through the filter cleaning port 412 in the direction of the ambient air filter 402 in order to clean the ambient air filter 402. In embodiments, the purge gas cylinder 414 may be a portable compressed air cylinder. Additionally, an end of an air supply line (now shown) may be connected to the purge gas cylinder 414 and another end of the air supply line may be positioned in or adjacent to the filter cleaning port 412. During the purge operation, the purge gas cylinder 414 may be automatically controlled, e.g., using a solenoid valve, which may enable the dispensing of the purge gas (e.g., compressed air) into the filter cleaning port 412. In embodiments, a timer may be utilized to activate a solenoid valve for dispensing the purge gas into the filter cleaning port 412. In additional embodiments, the purge gas cylinder 414 may be manually controlled to dispose the purge gas into the filter cleaning port 412.

It is noted that recitations herein of a component of the present disclosure being "configured" or "programmed" in a particular way, to embody a particular property, or to function in a particular manner, are structural recitations, as opposed to recitations of intended use. More specifically, the references herein to the manner in which a component is "configured" or "programmed" denotes an existing physical condition of the component and, as such, is to be taken as a definite recitation of the structural characteristics of the component.

Having described the subject matter of the present disclosure in detail and by reference to specific embodiments thereof, it is noted that the various details disclosed herein should not be taken to imply that these details relate to elements that are essential components of the various embodiments described herein, even in cases where a particular element is illustrated in each of the drawings that accompany the present description. Further, it will be apparent that modifications and variations are possible without departing from the scope of the present disclosure, including, but not limited to, embodiments defined in the appended claims. More specifically, although some aspects of the present disclosure are identified herein as preferred or particularly advantageous, it is contemplated that the present disclosure is not necessarily limited to these aspects.

It is noted that one or more of the following claims utilize the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising."

What is claimed is:

1. A universal safety guard comprising a calibration housing and a calibration valve assembly, wherein:
   the calibration housing comprises an adapter coupling end, a dual mode chamber, a calibration gas port, and an ambient air end comprising an ambient air aperture;
   the dual mode chamber of the calibration housing is located between the adapter coupling end and the ambient air end of the calibration housing;
   the calibration valve assembly is disposed in the dual mode chamber of the calibration housing and is configurable in a sensing position and a calibration position;
   the calibration valve assembly, when configured in the sensing position, admits ambient air through the ambient air aperture into the dual mode chamber and, when configured in the calibration position, admits calibration gas into the dual mode chamber, through the calibration gas port, and blocks the ambient air from reaching the dual mode chamber;
   the universal safety guard further comprises a detector adapter that comprises a hermetic gas passage body portion extending from a calibration housing fitting at one end of the detector adapter to a gas detector fitting at an opposite end of the detector adapter;
   the calibration housing fitting comprises a static circumferential sealing interface that hermetically engages the adapter coupling end of the calibration housing; and
   the gas detector fitting comprises a dynamic inner circumferential sealing interface for hermetic engagement with a gas detector comprising an outer sealing interface that complements the dynamic inner circumferential sealing interface of the gas detector fitting.

2. The universal safety guard of claim 1, wherein the hermetic gas passage body portion of the detector adapter steps down from a larger diameter portion at the calibration housing fitting to a smaller diameter portion at the gas detector fitting, or from a larger diameter portion at the gas detector fitting to a smaller diameter portion at the calibration housing fitting.

3. The universal safety guard of claim 2, wherein the hermetic gas passage body portion of the detector adapter comprises a uniform elastomeric polymer composition extending from the calibration housing fitting to the gas detector fitting.

4. The universal safety guard of claim 1, wherein the calibration housing fitting and the adapter coupling end of the calibration housing comprise complementary threaded portions.

5. The universal safety guard of claim 1, wherein the dynamic inner circumferential sealing interface of the gas detector fitting comprises an expandable sleeve that transitions from a resting state to an expanded state where the gas detector fitting exerts an inwardly directed radial force.

6. The universal safety guard of claim 5, wherein the expansion of the expandable sleeve of the gas detector fitting is isolated from the static circumferential sealing interface of the calibration housing fitting, such that diametrical changes at the dynamic inner circumferential sealing interface do not translate into diametrical changes at the static circumferential sealing interface.

7. The universal safety guard of claim 5, wherein the resting state of the expandable sleeve is characterized by an inside diameter that is less than about 5.5 cm.

8. The universal safety guard of claim 5, wherein the resting state of the expandable sleeve is characterized by an inside diameter that is between about 2.5 cm and about 5.5 cm.

9. The universal safety guard of claim 5, wherein the universal safety guard further comprises an adjustable ring clamp comprising a maximum clamping diameter that is larger than an outside diameter of the gas detector fitting in the expanded state, and a minimum clamping diameter that is smaller than the outside diameter of the gas detector fitting in the resting state.

10. The universal safety guard of claim 1, wherein:
the universal safety guard further comprises a ring clamp that is configured to deliver an inwardly directed radial clamping force; and
the dynamic inner circumferential sealing interface of the gas detector fitting comprises a compressible sleeve that transitions from a resting state to a compressed state under the inwardly directed radial clamping force of the ring clamp.

11. The universal safety guard of claim 10, wherein compression of the compressible sleeve of the gas detector fitting is isolated from the static circumferential sealing interface of the calibration housing fitting, such that diametrical changes at the dynamic inner circumferential sealing interface do not translate into diametrical changes at the static circumferential sealing interface.

12. The universal safety guard of claim 10, the universal safety guard further comprises an adjustable ring clamp comprising a maximum clamping diameter that is larger than an outside diameter of the gas detector fitting in the resting state.

13. The universal safety guard of claim 1, wherein:
the calibration valve assembly comprises a spring-loaded rod and plug assembly;
the spring-loaded rod and plug assembly comprises a calibration gas plug and an ambient air plug positioned on opposite ends of a spring-loaded valve rod;
the spring-loaded valve rod and the calibration gas plug move along a valve passage to selectively admit the calibration gas through a calibration gas admittance window of the valve passage; and
the spring-loaded valve rod is configured to advance the ambient air plug into engagement with a valve stop between the ambient air aperture and the dual mode chamber to block the ambient air while the calibration gas plug is positioned to admit the calibration gas through the calibration gas admittance window of the valve passage.

14. The universal safety guard of claim 1, wherein:
the universal safety guard further comprises an ambient air filter, a proximity sensor, and a filter maintenance controller;
the ambient air filter is positioned upstream of the ambient air aperture, between the dual mode chamber and the ambient air aperture, or downstream of the ambient air aperture;
the proximity sensor is positioned upstream of the ambient air filter, between the dual mode chamber and the ambient air filter and is configured to measure a distance between a control position upstream of the ambient air filter and an obstructed position downstream of the control position;
the proximity sensor is configured to generate an obstruction signal that indicates an air flow obstruction downstream of the control position, and transmit the obstruction signal to the filter maintenance controller; and
the filter maintenance controller is configured to generate an obstruction alert upon receiving the obstruction signal indicating the air flow obstruction downstream of the control position, in a vicinity of the ambient air filter.

15. The universal safety guard of claim 14, wherein the obstruction alert is an audio alert, a visual alert, or an alert that is transmitted over a communications link.

16. The universal safety guard of claim 14, wherein:
the universal safety guard further comprises a filter cleaning port in communication with a supply of purge gas; and
the obstruction alert generated by the filter maintenance controller initiates a purge operation where purge gas is transmitted through the filter cleaning port in a direction of the ambient air filter to clean the ambient air filter.

17. The universal safety guard of claim 14, wherein the proximity sensor is an optical or sound-based sensor.

18. A universal safety guard comprising a calibration housing and a calibration valve assembly, wherein:
the calibration housing comprises an adapter coupling end, a dual mode chamber, a calibration gas port, and an ambient air end comprising an ambient air aperture;
the dual mode chamber of the calibration housing is located between the adapter coupling end and the ambient air end of the calibration housing;
the calibration valve assembly is disposed in the dual mode chamber of the calibration housing and is configurable in a sensing position and a calibration position;
the calibration valve assembly, when configured in the sensing position, admits ambient air through the ambient air aperture into the dual mode chamber and, when configured in the calibration position, admits calibration gas into the dual mode chamber, through the calibration gas port, and blocks the ambient air from reaching the dual mode chamber;
the calibration valve assembly comprises a spring-loaded rod and plug assembly;
the spring-loaded rod and plug assembly comprises a calibration gas plug and an ambient air plug positioned on opposite ends of a spring-loaded valve rod;
the spring-loaded valve rod and the calibration gas plug move along a valve passage to selectively admit the calibration gas through a calibration gas admittance window of the valve passage;

the spring-loaded valve rod is configured to advance the ambient air plug into engagement with a valve stop between the ambient air aperture and the dual mode chamber to block the ambient air while the calibration gas plug is positioned to admit the calibration gas through the calibration gas admittance window of the valve passage;

the universal safety guard further comprises an ambient air filter, a proximity sensor, and a filter maintenance controller;

the ambient air filter is positioned upstream of the ambient air aperture, between the dual mode chamber and the ambient air aperture, or downstream of the ambient air aperture;

the proximity sensor is positioned upstream of the ambient air filter, between the dual mode chamber and the ambient air filter and is configured to measure a distance between a control position upstream of the ambient air filter and an obstructed position downstream of the control position;

the proximity sensor is configured to generate an obstruction signal that indicates an air flow obstruction downstream of the control position, and transmit the obstruction signal to the filter maintenance controller;

the filter maintenance controller is configured to generate an obstruction alert upon receiving the obstruction signal indicating the air flow obstruction downstream of the control position, in a vicinity of the ambient air filter;

the universal safety guard further comprises a detector adapter that comprises a hermetic gas passage body portion extending from a calibration housing fitting at one end of the detector adapter to a gas detector fitting at an opposite end of the detector adapter, the hermetic gas passage body portion of the detector adapter steps down from a larger diameter portion at the calibration housing fitting to a smaller diameter portion at the gas detector fitting, or from a larger diameter portion at the gas detector fitting to a smaller diameter portion at the calibration housing fitting;

the calibration housing fitting comprises a static circumferential sealing interface that hermetically engages the adapter coupling end of the calibration housing;

the gas detector fitting comprises a dynamic inner circumferential sealing interface for hermetic engagement with a gas detector comprising an outer sealing interface that complements the dynamic inner circumferential sealing interface of the gas detector fitting, the dynamic inner circumferential sealing interface of the gas detector fitting comprises an expandable sleeve that transitions from a resting state to an expanded state where the gas detector fitting exerts an inwardly directed radial force, and the expansion of the expandable sleeve of the gas detector fitting is isolated from the static circumferential sealing interface of the calibration housing fitting, such that diametrical changes at the dynamic inner circumferential sealing interface do not translate into diametrical changes at the static circumferential sealing interface.

19. The universal safety guard of claim 18, wherein the hermetic gas passage body portion of the detector adapter comprises a uniform elastomeric polymer composition extending from the calibration housing fitting to the gas detector fitting.

20. The universal safety guard of claim 18, wherein the resting state of the expandable sleeve is characterized by an inside diameter that is less than about 5.5 cm.

\* \* \* \* \*